US009340585B2

(12) United States Patent
Gardan et al.

(10) Patent No.: US 9,340,585 B2
(45) Date of Patent: May 17, 2016

(54) COMPETENCE STIMULATING PEPTIDE (71) Applicant: INSTITUT NATIONAL DE LA RECHERCHE AGRONOMIQUE, Paris (FR)

(72) Inventors: Rozenn Gardan, Jouy-en-Josas (FR); Veronique Monnet, Montigny-le-bretonneux (FR)

(73) Assignee: Institut National De La Recherche Agronomique, Paris (FR)

(*) Notice: Subject to any disclaimer, the term of this patent is extended or adjusted under 35 U.S.C. 154(b) by 0 days.

(21) Appl. No.: 14/327,422

(22) Filed: Jul. 9, 2014

(65) Prior Publication Data
US 2014/0322718 A1 Oct. 30, 2014

Related U.S. Application Data (62) Division of application No. 13/266,103, filed as application No. PCT/EP2010/055692 on Apr. 28, 2010, now abandoned.

(30) Foreign Application Priority Data

Apr. 28, 2009 (EP) .................................. 09305367

(51) Int. Cl.
  *C07K 14/315* (2006.01)
  *C12N 1/20* (2006.01)
  *C12N 15/74* (2006.01)
(52) U.S. Cl.
  CPC ................ *C07K 14/315* (2013.01); *C12N 1/20* (2013.01); *C12N 15/746* (2013.01)
(58) Field of Classification Search
  CPC .................................................... C07K 14/315
  See application file for complete search history.

(56) References Cited

U.S. PATENT DOCUMENTS

| 5,916,876 | A  | 6/1999  | Heavner et al.      |
| 6,800,744 | B1 | 10/2004 | Doucette-Stamm et al. |
| 7,393,663 | B2 | 7/2008  | Edwards et al.      |
| 8,663,655 | B2 | 3/2014  | Boyaval et al.      |
| 2005/0136404 | A1 | 6/2005 | Doucette-Stamm et al. |
| 2009/0144848 | A1 | 6/2009 | Kovalic et al.      |
| 2012/0129264 | A1 | 5/2012 | Boyaval et al.      |

FOREIGN PATENT DOCUMENTS

| EP | 2 248 823     | 11/2010 |
| EP | 2 424 883     | 3/2012  |
| EP | 2 445 929     | 5/2012  |
| WO | WO 2006/060903 | 6/2006  |
| WO | WO 2007/129072 | 11/2007 |
| WO | WO 2010/125091 | 11/2010 |
| WO | WO 2010/149721 | 12/2010 |

OTHER PUBLICATIONS

Blomqvist et al. (Aug. 2006) "Pheromone-induced expression of recombinant proteins in *Streptococcus thermophiles*," *Arch Microbiology*. 186(6):465-73 (epub Aug. 2006).
U.S. Appl. No. 14/162,398, filed Jan. 23, 2014, Boyaval et al.
U.S. Appl. No. 61/239,896, filed Sep. 4, 2009, Boyaval et al.
U.S. Appl. No. 61/219,436, filed Jun. 23, 2009, Boyaval et al.
Cvitkovitch et al. (2008) "Quorum sensing and biofilm formation by *Streptococcus mutans*," *Advances in Experimental Medicine and Biology—Bacterial Signal Transduction: Networks and Drug Targets*. vol. 631 pp. 178-188.
Gardan et al. (Jul. 2009) "The Oligopeptide Transport System Is Essential for the Development of Natural Competence in *Streptococcus thermophilus* Strain LMD-9," *Journal of Bacteriology*. 191(14):4647-4655.
International Preliminary Report on Patentability corresponding to International Patent Application No. PCT/EP2010/055692, completed Nov. 1, 2011.
International Search Report with Written Opinion corresponding to International Patent Application No. PCT/EP2010/055692, mailed Jun. 29, 2010.
Johnsborg et al. (Mar. 2006) "A hydrophobic patch in the competence-stimulating peptide, a pneumococcal competence pheromone, is essential for specificity and biological activity," *Journal of Bacteriology*. 188(5):1744-1749.
Lawson et al. (Jun. 1970) "Growth and development of competence in the group H streptococci," *Journal of Bacteriology*. 102(3):820-825.
Peterson et al. (Dec 2003) "Identification of competence pheromone responsive genes in *Streptococcus pneumonia* by use of DNA microarrays," *Mol. Microbiology*. 51:1051-1070.
Bachmann et al. (2008) "High-throughput identification and validation of in situ-expressed genes of Lactococcus lactis," *Applied Environmental Microbiology*. 74:4727-4736.
Barbe et al. (2004) "Unique features revealed by the genome sequence of *Acinetobacter* sp. ADPI, a versatile and naturally transformation competent bacterium," *Nucleic Acids Research*. 32(19):5766-5779.
Bolotin et al. (2004) "Complete sequence and comparative genome analysis of the dairy bacterium *Streptococcus thermophilus*," *Nat. Biotechnology*. 22:1554-1558.
Bouillaut et al. (2008) "Molecular Basis for Group-Specific Activation of the Virulence Regulator PlcR by PapR Heptapeptides," *Nucleic Acid Research*. 36(11):3791-3801.
Claverys et al. (2003) "Bacterial 'competence' genes: signatures of active transformation, or only remnants?" *Trends Microbiol*. 11:161-165.

(Continued)

Primary Examiner — Amber D Steele
(74) Attorney, Agent, or Firm — Lathrop & Gage LLP (57) ABSTRACT

The present invention concerns a new competence stimulating peptide identified in *Firmicutes*, in particular *Streptococcus*, and more preferably *S. thermophilus* and methods of producing transformation competent *Firmicutes*, in particular *Streptococcus*, and more preferably *S. thermophilus* bacteria.

18 Claims, 3 Drawing Sheets

(56) References Cited

OTHER PUBLICATIONS

Claverys et al. (2006) "Induction of competence regulons as a general responses to stress in gram-positive bacteria," *Annu. Rev. Microbiol.* 60:451-475.

Database GenBank Accession No. CAA66786. Competence Pheromone [*Streptococcus gordonii*]. Apr. 18, 2005.

Database UniProt Accession No. Q6FB69. Jul. 19, 2004.

Eddy (2004) "Where did he BLOSUM62 alignment score matrix come from?" *Nature Biotechnology.* 22:1035-1036.

Fernandez-Espla et al. (2000) "*Streptococcus thermophilus* cell all-anchored proteinase: release, purification, and biochemical and genetic characterization," *Applied Environ. Microbiol.* 66:4772-4778.

Fontaine et al. (2007) "Quorum sensing regulation of the production of Bpl bacteriocins in *Streptococcus thermophilus*," *J. Bacteriol.* 189:7195-7205.

Hols et al. (2005) "New insights in the molecular biology and physiology of *Streptococcus thermophilus* revealed by comparative genomics," *FEMS Microbiology Review.* 29(3):435-463.

Huggins et al. (1984) "Differentiation of fast and slow milk-coagulating isolates in strains of lactic Streptococci," *J. Dairy Science.* 67:1674-1679.

Ibrahim et al. (2007) "Control of the transcription of a short gene encoding a cyclic peptide in *Streptococcus thermophilus*: a new quorum-sensing system?" *J. Bacteriol.* 189:8844-8854.

International Preliminary Report on Patentability corresponding to International Patent Application No. PCT/EP2010/058947, completed Jan. 4, 2012.

International Search Report with Written Opinion corresponding to International Patent Application No. PCT/EP2010/058947, mailed Aug. 23, 2010.

Knutsen et al. (2004) "Two separate quorum-sensing systems upregulate transcription of the same ABC transporter in *Streptococcus pneumonia*," *Journal of Bacteriology.* 186(10):3078-3085.

Kozlowicz et al. (2006) "Molecular basis for control of conjugation by bacterial pheromone and inhibitor peptides," *Mol. Microbiol.* 62:958-869.

Lambert et al. (2007) "Cre-lox-based system for multiple gene deletions and selectable-marker removal in Lactobacillus plantarum," *Appl. Environ. Microbiol.* 73:1126-1135.

Maguin et al. (1992) "New thermosensitive plasmid for gram-positive bacteria," *Journal of Bacteriology.* 174:5633-5638.

Maguin et al. (1996) "Efficient insertional mutagenesis in lactococci and other gram-positive positive bacteria," *Journal of Bacteriology.* 178:931-935.

Makarova et al. (2006) "Comparative genomics of the lactic acid bacteria," *Proc. Natl. Acad. Sci. USA.* 103:15611-15616.

Martin et al. (2006) "Independent evolution of competence regulatory cascades in streptococci?" *Trends Microbiol.* 14:339-345.

Perego et al. (2001) "Pentapeptide Regulation of Aspartyl-Phosphate Phosphates," *Peptides.* 22:1541-1547.

Slamti et al. (2002) "A cell-cell signaling peptide activates the PlcR virulence regulon in bacteria of Bacillus cereus group," *EMBO J.* 21:4550-4559.

Slamti et al. (Feb. 2005) "Specificity and Polymorphism of the PlcR-PapR Quorum-Sensing System in the Bacillus cereus Group," *Journal of Bacteriology.* 187(3):1182-1187.

Spinnler et al. (1989) "Automatic method to quantify starter activity based on pH measurement," *J. Dairy Research.* 56:755-764.

COMPETENCE STIMULATING PEPTIDE

CROSS-REFERENCE TO RELATED APPLICATIONS

This application is a divisional of U.S. patent application Ser. No. 13/266,103, filed Oct. 24, 2011, which is a U.S. National Stage application of International Application No. PCT/EP2010/055692, filed in English on Apr. 28, 2010, which designates the United States and which was also published in English, and which claims the benefit of European Patent Application No. 09305367.6, filed in English on Apr. 28, 2009. Each of these applications is incorporated by reference herein in its entirety.

DOMAIN OF THE INVENTION

The present invention relates to Firmicutes, in particular Streptococcus, and more preferably S. thermophilus competence, and more specifically to a new competence stimulating peptide.

BACKGROUND OF THE INVENTION

Many species of bacteria control gene expression on a community-wide scale by producing, secreting, detecting and responding to extracellular signaling molecules (sometimes called 'autoinducers' or 'pheromones') that accumulate in the environment. This phenomenon is termed 'quorum sensing' (QS) as gene expression is triggered by the 'sensing' of the pheromone when its concentration has reached a 'quorum'. In Gram-positive bacteria, the signaling molecules are mainly short peptides acting either from the outside part of bacteria or from the inside, after internalization via oligopeptide transport systems called Opp or Ami.

Several bacterial functions such as the virulence in Staphylococcus aureus and Enterococcus faecalis, the competence in Bacillus subtilis or the production of bacteriocin in Lactococcus lactis are controlled by peptides acting at the surface of bacteria. However, the paradigm for mechanisms involving peptides detected from the outside is the regulation of the competence state for natural transformation by chromosomal donor DNA in Streptococcus pneumoniae. In this bacterium, the signaling peptide, called CSP (Competence Stimulating Peptide) and encoded by the gene comC, is secreted and matured by an ABC transporter, ComAB. The detection of the extracellular CSP at the surface of the bacterium is achieved by a two component system (TCS). Firstly, the membrane embedded histidine kinase, ComD, autophosphorylates in response to CSP and further phosphorylates its cognate response regulator, ComE, which activates transcription of a few genes, the early CSP-induced genes, including comCDE, comAB and comX. ComX is an alternative competence specific sigma factor required for expression of late CSP-induced genes, which comprise genes encoding the DNA uptake machinery.

Concerning signaling peptides that are active after internalization by an oligopeptide transporter, three groups have been described in detail: (i) Phr peptides in B. subtilis involved in the control of sporulation, competence, and production of degradative enzymes and antibiotics, (ii) PapR peptides involved in the control of virulence of bacteria belonging to the Bacillus cereus group and (iii) peptides involved in the control of plasmid transfer in Enterococcus faecalis. All these extracellular short peptides interact with either Rap phosphatases (in B. subtilis) or transcriptional regulators (PlcR in B. cereus or PrgX in E. faecalis) to elicit a physiological response.

Oligopeptide transport systems involved in these signaling pathways belong to the superfamily of ATP-binding cassette (ABC) transporters. They are composed of five subunits: an extracellular oligopeptide-binding protein, OppA that specifically captures the substrates, two transmembrane proteins, OppB and OppC that form the pore and two membrane-bound cytoplasmic ATP-binding proteins, OppD and OppF that provide the energy for peptide translocation. Several copies of the opp operon and/or of the genes encoding the oligopeptide-binding proteins can be present in a single genome. The genome of Streptococcus thermophilus encodes one oligopeptide transport system and depending on the strain, two (strain LMD-9 and CNRZ1066) or three (strain LMG18311) oligopeptide-binding proteins. In Gram-positive bacteria, two main functions have been attributed to the Opp transporters: nutrition and sensing. The nutritional role has been well studied in lactic acid bacteria such as Lactococcus lactis or S. thermophilus. During growth in milk, the Opp transporters supply these auxotrophic bacteria with peptides that serve as amino acid sources. The sensing function is more complex and is poorly documented, particularly in nonpathogenic bacteria.

Among the nonpathogenic bacteria, S. thermophilus is of major importance for the food industry since it is massively used for the manufacture of yoghurt and Swiss or Italian-type cheeses with an annual market value of approximately $40 billion making S. thermophilus a species of major economic importance. The industry is continuously working to improve the properties of S. thermophilus starter strains. Even though the fermentation properties of this bacterium have been gradually improved by classical methods, there is great potential for further improvement through genetic engineering.

However, until now, only genetic tools based on genetically modified bacteria exist. For example, Havarstein has disclosed an inducible system (stb system) that permits the surexpression of proteins in S. thermophilus (Blomgvist T. et al "Pheromone-induced expression of recombinant proteins in Streptococcus thermophilus" Arch Microbiol. 2006 December; 186(6):465-73. Epub 2006 Aug. 24.). In particular, this article discloses that a possible peptide-pheromone (STP) regulates bacteriocin production in S. thermophilus LMG 18311, and shows that the StbABCHR (system that regulates bacteriocin production) quorum-sensing system can be exploited for inducible expression of recombinant proteins in this bacterial species.

Thus, there is a need for an efficient method that allows obtaining improved Firmicutes, in particular Streptococcus, and more preferably S. thermophilus by natural processes of gene transfer, and not artificial gene transfer. This is particularly important for the food industries, for example the dairy industries which do not want to use GMO in their products.

Regarding this need of genetic tools, competence is poorly understood in S. thermophilus. In fact, regarding QS systems, only one of them has been yet described, which QS system (called stb or blp) controls the production of a bacteriocin.

The sequencing of the genome of three strains of S. thermophilus, CNRZ1066, LMG18311 and LMD-9, has revealed the presence of comX and of 14 proteins with strong similarities with the 14 proteins known to be required for competence in S. pneumoniae and encoded by late CSP-induced genes (Bolotin et al., Complete sequence and comparative genome analysis of the dairy bacterium Streptococcus thermophilus., Nat. Biotechnol. 22:1554-1558, 2004; Makarova et al. Comparative genomics of the lactic acid bacteria. *Proc Natl Acad Sci USA.*, 103(42):15611-6, 2006). Except comX, no ortholog of the early CSP-induced genes of *S. pneumoniae* have been detected in the genome of *S. thermophilus*. It has been shown that overexpression of comX induces the competent state in *S. thermophilus* LMG18311.

Still, how transformation is turned on in this strain and what regulatory pathway and more especially which competence stimulating peptide (CSP) controls the expression of comX have not previously been explained.

SUMMARY OF THE INVENTION

The present invention relates to an isolated polypeptide comprising the amino acids sequence SEQ ID No1 (LKTLKIFVLFSLLIAILPYFAGCL), or derivatives or fragments thereof capable of stimulating competence in *Firmicutes*, in particular *Streptococcus*, and more preferably *S. thermophilus*.

The present invention also relates to an isolated polypeptide comprising the amino acid sequence SEQ ID No7 (IAILPYFAGCL) or derivatives or fragments thereof capable of stimulating competence in *Firmicutes*, in particular *Streptococcus*, and more preferably *S. thermophilus*.

The present invention also relates to an isolated nucleic acid encoding for said isolated polypeptides.

The present invention still relates to a vector comprising said nucleic acid operably linked to a gene expression sequence.

The present invention still relates to a host cell genetically engineered with said vector.

The present invention also relates to a culture medium comprising an effective amount of said isolated polypeptide and nutrients that allow the growing of *Firmicutes*, in particular *Streptococcus*, and more preferably *S. thermophilus*.

The present invention further relates to a use of said polypeptide, said nucleic acid, said vector, said host cell, or said culture medium for stimulating competence in *Firmicutes*, in particular *Streptococcus*, and more preferably *S. thermophilus*.

The present invention still relates to a method of producing transformation competent *Firmicutes*, in particular *Streptococcus*, and more preferably *S. thermophilus* bacteria comprising the step (i) of contacting said *Firmicutes*, in particular *Streptococcus*, and more preferably *S. thermophilus* bacteria with an effective amount of an isolated polypeptide as defined in any one of claims 1 to 5 for obtaining said transformation competent *Firmicutes*, in particular *Streptococcus*, and more preferably *S. thermophilus* bacteria.

DETAILED DESCRIPTION OF THE INVENTION

Surprisingly, the inventors have established that the Ami oligopeptide transport system is implicated in the control of competence in *Streptococcus*, in particular *S. thermophilus*. This transport system functions with several oligopeptide binding proteins. In strain LMD9 where two oligopeptide binding proteins are present, AmiA3 and AmiA1, AmiA3 plays the major role in the control of competence.

More specifically, the inventors have identified one new polypeptide and fragments thereof implicated in the control of competence.

In a first aspect, the present invention relates to an isolated polypeptide comprising the amino acids sequence SEQ ID No1 (LKTLKIFVLFSLLIAILPYFAGCL), or derivatives or fragments thereof capable of stimulating competence in *Firmicutes*, in particular *Streptococcus*, and more preferably *S. thermophilus*.

The isolated polypeptide of the invention has the ability to stimulate the competence in *Firmicutes*, in particular *Streptococcus*, and more preferably *S. thermophilus* strains.

According to the present invention, the length of the isolated polypeptide of the invention is less than 100 amino acids, preferably less than 50 amino acids.

In a preferred embodiment, the isolated polypeptide of the present invention consists in the amino acids sequence SEQ ID No1 (LKTLKIFVLFSLLIAILPYFAGCL), or derivatives or fragments thereof, said derivatives and fragments being capable of stimulating competence in *Firmicutes*, in particular *Streptococcus*, and more preferably *S. thermophilus*.

In another preferred embodiment, the isolated polypeptide of the present invention comprises, preferably consists in, a fragment of the amino acids sequence SEQ ID No1 capable of stimulating competence in *Firmicutes*, in particular *Streptococcus*, and more preferably *S. thermophilus*.

In still another embodiment, the isolated polypeptide of the present invention comprises, preferably consists in, the amino acids sequence SEQ ID No7 (IAILPYFAGCL) or derivatives or fragments thereof, said derivatives and fragment being capable of stimulating competence in *Firmicutes*, in particular *Streptococcus*, and more preferably *S. thermophilus*.

As used herein, the term "fragment" refers to the products of the chemical, enzymatic, or physical breakdown of a polypeptide. Such fragments may for example be obtained through enzymatic reaction, such as degradation by protease and/or aminopeptidases.

Preferably, the length of such fragment is comprised between 3 and 17 amino acids, preferably from 4 to 15 amino acids, and more preferably from 6 to 12 amino acids.

In another preferred embodiment, the isolated polypeptide of the present invention further comprises an amino acid sequence corresponding to a signal peptide.

Said signal peptide allows the secretion of the polypeptide of the invention in the extracellular medium when said polypeptide is expressed in a prokaryotic or an eukaryotic cell, preferably in a prokaryotic cell, such as in a bacteria from the *Streptococcus* genus, more preferably in a *Firmicutes*, in particular *Streptococcus*, and more preferably *S. thermophilus* bacteria.

Such signal peptides are well known from the skilled person.

As used herein, the term "derivatives'" refer to an amino acid sequence having a percentage of identity of at least 70% with the amino acid sequence SEQ ID N°:1, as an example at least 85% (i.e. 3 amino acids substitution), preferably of at least 90% (i.e. 2 amino acids substitution), and more preferably of at least 95% (i.e. 1 amino acids substitution).

As an example of derivative, one can cite the polypeptide of sequence SEQ ID No5 (MGKTLKIFVLFSLLIAILPYF-AGCL), which is disclosed in the examples.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compared the local regions of similarity. The best sequences alignment to perform comparison can be realized, beside by a manual way, by using computer software using such algorithms (GAP, BESTFIT, BLAST P, BLAST N, FASTA, TFASTA). The identity percentage between two sequences of amino acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences As used herein an amino acid sequence having the ability to stimulate the competence in *Firmicutes*, in particular *Streptococcus*, and more preferably *S. thermophilus* strains can simply be identified by one of skilled in the art in view of the following examples. As an example, the skilled person can screen for polypeptides derived from SEQ ID No1 inducing competence in *Firmicutes*, in particular *Streptococcus*, and more preferably *S. thermophilus* when present in the culture medium.

It will also be understood that natural amino acids may be replaced by chemically modified amino acids. Typically, such chemically modified amino acids enable to increase the polypeptide half life.

In a second aspect the present invention relates to an isolated nucleic acid encoding for the isolated polypeptide as described above.

Said nucleic acid corresponds to RNA or DNA, preferably to DNA.

According to a preferred embodiment, said isolated nucleic acid comprises a nucleic acid sequence selected in the group comprising

```
                                          (SEQ ID No 2)
TTGAAAACCCTGAAAATATTTGTACTATTTTCACTACTTATTGCT

ATCTTGCCTTATTTTGCAGGATGTCTTTAA
and
                                          (SEQ ID No 6)
ATGGGGAAAACCCTGAAAATATTTGTACTATTTTCACTACTTATTG

CTATCTTGCCTTATTTTGCAGGATGTCTTTAA.
```

In a third aspect, the present invention relates to a vector comprising the nucleic acid encoding for the isolated polypeptide of the invention as described above operably linked to a gene expression sequence.

Said gene expression sequence directs the expression of said nucleic acid within a prokaryotic or an eukaryotic cell, preferably within a prokaryotic cell, and more preferably within *Firmicutes*, in particular *Streptococcus*, and more preferably *S. thermophilus* bacteria. The "gene expression sequence" is any regulatory nucleotide sequence, such as a promoter sequence or promoter-enhancer combination, which facilitates the efficient transcription and translation of the nucleic acid to which it is operatively linked. The gene expression sequence may be a constitutive or inducible promoter.

Such promoters are well known in the art. Promoters for use in the invention are preferably strong promoters, i.e. on induction in the relevant cell yield high levels of transcription of the downstream gene. Examples of strong inducible promoters include by examples promoters, from bacteria, involved in the production of bacteriocins such as the stb promoter.

In general, the gene expression sequence shall include, as necessary, 5' non-transcribing and 5' non-translating sequences involved with the initiation of transcription and translation, respectively. The gene expression sequences optionally include enhancer sequences or upstream activator sequences as desired.

As used herein, the nucleic acid sequence encoding the polypeptide of the invention and the gene expression sequence are said to be "operably linked" when they are covalently linked in such a way as to place the expression or transcription and/or translation of the polypeptide of the invention coding sequence under the influence or control of the gene expression sequence. Two DNA sequences are said to be operably linked if induction of a promoter in the 5' gene expression sequence results in the transcription of the polypeptide of the invention and if the nature of the linkage between the two DNA sequences does not result in the introduction of a frame-shift mutation, interfere with the ability of the promoter region to direct the transcription of the polypeptide of the invention, or interfere with the ability of the corresponding RNA transcript to be translated into a protein. Thus, a gene expression sequence would be operably linked to a nucleic acid sequence coding for the polypeptide of the invention if the gene expression sequence was capable of effecting transcription of that nucleic acid sequence such that the resulting transcript is translated into the desired polypeptide.

Preferred vectors are plasmid vectors, which have been extensively described in the art and are well known to those of skilled in the art. See e.g., SaMbrook et al., "Molecular Cloning: A Laboratory Manual," Second Edition, Cold Spring Harbor Laboratory Press, 1989.

The vector of the invention can include a selectable marker that is active in bacteria.

In a forth aspect, the present invention relates to a host cell genetically engineered with the vector described previously.

As used herein, the term "host cell genetically engineered" relates to host cells which have been transformed with the vector described previously.

Said host cell is preferably a bacterial cell, such as a bacteria belonging to the *Firmicutes* phylum, preferably the *Streptoccous* genus, and more preferably a *Streptococcus thermophilus* bacteria.

The introduction of the vector described previously into the host cell can be effected by method well known from one of skilled in the art such as calcium phosphate transfection or electroporation.

In a fifth embodiment, the present invention relates to a culture medium comprising an effective amount of the isolated polypeptide as described above and nutrients that allow the growing of *Firmicutes*, in particular *Streptococcus*, and more preferably *S. thermophilus*.

According to the present invention, an "effective amount" of said isolated polypeptide is one which is sufficient to achieve a desired biological effect, in this case stimulating competence in Firmicutes, in particular Streptococcus, and more preferably S. thermophilus. As an example, said effective amount is comprised between 0.1 ng/ml and 1 mg/ml, preferably between 0.5 ng/ml and 1 mg/ml, and more preferably between 1 ng/ml and 100 ng/ml.

Nutrients of the culture medium are well known from the skilled person and include, as for example lactose, sodium acetate, ascorbic acid, potassium phosphate. Preferably, the medium culture does not contain any nutritional peptides, such as those provided by neopeptone or yeast extract.

There are numerous causes of peptide instability or degradation, including hydrolysis and denaturation. This result may entail diminution of the induction of the competence in Firmicutes, in particular Streptococcus, and more preferably S. thermophilus. Stabilizers may be added to lessen or prevent such problems.

According to a specific embodiment, the culture medium of the invention further comprises at least one stabilizer.

Stabilizers include cyclodextrin and derivatives thereof (see U.S. Pat. No. 5,730,969). Suitable preservatives such as sucrose, mannitol, sorbitol, trehalose, dextran and glycerin can also be added to stabilize the final formulation. Polyols may stabilize a peptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids.

In a sixth aspect, the present invention relates to the use of a polypeptide as described above, a nucleic acid as described previously, a vector comprising such a nucleic acid, a host cell as defined previously, or a culture medium as described previously for stimulating competence in Firmicutes, in particular Streptococcus, and more preferably S. thermophilus.

In a seventh aspect, the present invention relates to a method of producing transformation competent Firmicutes, in particular Streptococcus, and more preferably S. thermophilus bacteria comprising the step (i) of contacting said Firmicutes, in particular Streptococcus, and more preferably S. thermophilus bacteria with an effective amount of an isolated polypeptide as defined previously for obtaining said transformation competent Firmicutes, in particular Streptococcus, and more preferably S. thermophilus bacteria.

Preferably, the method of the invention is performed in a culture medium as described previously.

In a eight aspect, the present invention relates to a method of producing transformation competent Firmicutes, in particular Streptococcus, and more preferably S. thermophilus bacteria comprising the step (i) of culturing said Firmicutes, in particular Streptococcus, and more preferably S. thermophilus bacteria in a peptide free medium allowing the growth of said bacteria to an OD600 comprised between 1.5 and 2.5 preferably about 2 and (i') diluting said culture to an OD600 comprised between 0.01 and 0.1, preferably about 0.05.

Preferably, the present invention relates to a method of producing transformation competent Firmicutes, in particular Streptococcus, and more preferably S. thermophilus bacteria comprising the step (i) of culturing said Firmicutes, in particular Streptococcus, and more preferably S. thermophilus bacteria in M17 lactose (10 g/l) for 8 hours and (i') diluting said culture 50 fold in a peptide free medium. The diluted culture is then incubated at 4° C. for 10 hours and further incubated at 42° C. for 6 hours allowing the growth of said bacteria to an OD600 comprised between 1.5 and 2.5 preferably about 2, and (i") diluting said culture in a peptide free medium to an OD600 comprised between 0.01 and 0.1, preferably about 0.05.

For example, said peptide free medium comprises:

|  | g/mol | g/l |
|---|---|---|
| Lactose/Buffer | | |
| lactose | 360.32 | 10 g |
| Na acetate | 82.03 | 1 g |
| ammonium citrate | 243.2 | 0.6 g |
| KH2PO4 | 136.09 | 3 g |
| K2HPO4 | 174.18 | 2.5 g |
| urea | 60.06 | 0.240 g |
| Vitamins | | |
| 1 Ascorbic acid L+ | 176.13 | 0.5 g |
| 2 pyridoxamin | 241.1 | 5 mg |
| 3 nicotinic acid | 123.1 | 1 mg |
| 4 riboflavin | 376.4 | 1 mg |
| 5 panthothenic acid | 238.3 | 1 mg |
| 6 thiamin | 337.3 | 1 mg |
| 7 pyridoxin | 205.6 | 2 mg |
| 8 aminobenzoic acid | 137.1 | 10 mg |
| 9 biotin | 244.3 | 10 mg |
| 10 folic ac | 441.4 | 1 mg |
| 11 B12 | 1355.4 | 1 mg |
| 12 orotic ac | 156.1 | 5 mg |
| 13 thymidine | 242.2 | 5 mg |
| 14 inosin | 268.23 | 5 mg |
| 15 DL 6,8 thioctic ac | 206.3 | 2.5 mg |
| Metals | | |
| MgCL2—6H2O | 203.3 | 0.200 g |
| CaCL2—2H2O | 147.02 | 0.050 g |
| FeCl2 | 198.81 | 0.005 g |
| ZnSO4 | 287.54 | 0.005 g |
| CuSO4 | 249.7 | 0.000 g |
| CoCl2 | 237.9 | 0.003 g |
| MnSO4 | 169 | 0.028 g |
| Amino Acid | | |
| L aspartic acid | 133.1 | 0.455 g |
| L glutamic acid | 147.13 | 0.398 g |
| L asparagine | 132.1 | 0.350 g |
| L glutamine | 146.1 | 0.390 g |
| L histidine | 155.16 | 0.150 g |
| L arginine | 174.2 | 0.350 g |
| L lysine | 146.2 | 0.440 g |
| L serine | 105.1 | 0.225 g |
| L threonine | 119.1 | 0.175 g |
| glycine | 75.07 | 0.175 g |
| L alanine | 89.1 | 0.240 g |
| L isoleucine | 131.18 | 0.210 g |
| L leucine | 131.18 | 0.475 g |
| L valine | 117.1 | 0.325 g |
| L tryptophan | 204.2 | 0.050 g |
| L methionine | 149.2 | 0.125 g |
| L proline | 115.13 | 0.675 g |
| L phenylalanine | 165.19 | 0.275 g |
| L tyrosine | 181.2 | 0.290 g |
| L cysteine | 121.16 | 0.250 g |
| Nucleic acids | | |
| adenine | 135.1 | 0.010 g |
| uracil | 112.09 | 0.010 g |
| xanthine | 174.1 | 0.010 g |
| guanine | 187.6 | 0.010 g |

The medium is adjusted to pH 6.6 with HCl, completed to 1 L with water and filtered on GV filter.

Advantageously, said Firmicutes, in particular Streptococcus, and more preferably S. thermophilus bacteria is selected in the group comprising S. thermophilus LMD-9, S. thermophilus CNRZ1066 and S. thermophilus LMG18311, preferably S. thermophilus LMD-9.

According to a preferred embodiment, said methods are for producing a mutant bacteria and said method further comprises the step (ii) contacting said transformation competent Firmicutes, in particular Streptococcus, and more preferably S. thermophilus bacteria with homologous DNA under conditions to allow transformation of said bacteria with said homologous DNA and insertion of the homologous DNA in the chromosome of Firmicutes, in particular Streptococcus, and more preferably S. thermophilus by homologous recombination.

Said homologous DNA can be linear DNA (PCR fragment), plasmid DNA or chromosomal DNA.

Advantageously, said contacting step (ii) is realised simultaneously with the step (i') of diluting the culture of the method according to the eighth aspect. In that case, the transformation happened essentially during the 100 minutes following said contacting, more specifically essentially during the first 60 minutes.

Advantageously, said methods may comprise the steps (iii) of selecting and/or amplifying the mutant bacteria thus generated.

In a ninth aspect, the present invention concerns a method of screening a compound, preferably a polypeptide, capable of stimulating competence in Firmicutes, in particular Streptococcus, and more preferably S. thermophilus using the oligopeptide binding protein AmiA3 target and comprising the steps of contacting said compound with AmiA3, verifying the binding between AmiA3 and said compound, and selecting compound that bind to AmiA3 as a compound capable of stimulating competence in Firmicutes, in particular Streptococcus, and more preferably S. thermophilus.

Methods for verifying the binding between AmiA3 and said compound are well known by the skilled person.

In a tenth aspect, the present invention concerns a method for identifying a compound stimulating competence in Firmicutes, in particular Streptococcus, and more preferably S. thermophilus comprising the steps of:

i) contacting, with said compound, a host cell (preferably a bacteria) transformed with a nucleic acid comprising a nucleic acid sequence coding for a reporter protein (preferably GFP, beta Galactosidase, etc.) under the control of all or part of a promoter preceded by the inverted repeat sequence recognized by the PlcR like regulator (Ster0316 in strain LMD9, str0270 in strain CNRZ1066, stu0270 in strain LMG18311) ATAGTgacatatatgtctctat (SEQ ID No3) or gtg-gtgacataaatgtcactat (SEQ ID No4);

ii) selecting the compound that stimulates the expression of said reporter protein.

Methods for testing the stimulation of Firmicutes, in particular Streptococcus, and more preferably S. thermophilus competence are well known from the skilled person. Examples of such methods are disclosed in the examples.

In a preferred embodiment, the method of the invention can further comprises the steps of:

iii) contacting said compound with Firmicutes, in particular Streptococcus, and more preferably S. thermophilus in the presence of DNA (plasmids, chromosomal DNA, etc.); and iv) selecting the compounds that effectively enhance competence.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

1) The Ami Transporter Controls the Synthesis of Several Proteins Essential for Natural Transformation in Streptococci In order to find physiological functions controlled by signaling peptides that are internalized by the Ami transporter, we compared the proteome of the wild type LMD-9 strain and its isogenic mutant deleted for the ami operon, LMD-9 ΔamiCDE (TIL883; Ibrahim et al., J. Bacteriol., vol. 189, p: 8844-8854, 2007).

In order to by-pass the nutritional function of the Ami transporter, cells were gown in CDM, a free-peptide chemically defined medium (CDM), containing only amino acids as nitrogen source, as described by Letort & Juillard, Development of a minimal chemically-defined medium for the exponential growth of Streptococcus thermophilus, J. Appl. Microbiol., vol. 91., p. 1023-1029, 2001. Optical density at 600 nm ($OD_{600}$) of the cultures was measured using a spectrophotometer UVIKON 931 (KONTRON).

Proteins were prepared from cells grown in CDM and harvested at $OD_{600}$ 0.7 in two independent cultures for each strain. Bacteria were mechanically disrupted and the supernantants were ultracentrifuged at 220, 000 g for 30 min at 4° C. to enrich the 'cell envelope pellets' in cell-envelope proteins. Finally the pellet were resuspended in disruption buffer and sonicated for 15 min at 4° C. in an ultrasonic bath. The cell-envelope pellet fractions (10 μg) were separated by 1D electrophoresis. Each 1D electrophoresis lane was cut into 26 pieces of gel (2 mm width). In-gel digestion of the proteins was performed with the Progest system (Genomic Solution) according to the following protocol.

Gel pieces were washed firstly, in two successive baths of (i) 10% acetic acid 40% ethanol and (ii) 100% acetonitrile (ACN) and secondly, in two successive baths of (i) 25 mM NH4CO3 and (ii) 100% ACN. Gel pieces were further incubated in 10 mM DTT in 25 mM NH4CO3, 30 min at 55° C. and in 50 mM iodoacetamide in 25 mM NH4CO3, 45 min at room temperature for cysteine reduction and alkylation, respectively. Digestion was subsequently performed for 6 h at 37° C. with 125 ng of modified trypsin (PROMEGA) dissolved in 20% methanol and 20 mM NH4CO3, per gel piece. The peptides were extracted successively with (i) 0.5% trifluoroacetic acid (TFA) 50% ACN and (ii) with 100% ACN. The resulting peptide extracts were dried in a vacuum centrifuge and suspended in 25 μl of 0.08% TFA, and 2% ACN.

Fractions enriched in cell envelope proteins were then analyzed by a label-free comparative proteomic approach combining 1D electrophoresis with LC-MS/MS analysis.

LC-MS/MS analysis was performed on Ultimate 3000 LC system (DIONEX) connected to LTQ Orbitrap mass spectrometer (Thermo Fisher) by nanoelectrospray ion source. Tryptic peptide mixtures (4 μl) were loaded at flow rate 20 μl min-1 onto precolumn Pepmap C18 (0.3×5 mm, 100 Å, 5 μm; DIONEX). After 4 min, the precolumn was connected with the separating nanocolumn Pepmap C18 (0.075×15 cm, 100 Å, 3 μm) and the linear gradient was started from 2 to 36% of buffer B (0.1% formic acid, 80% acetonitrile) in buffer A (0.1% formic acid, 2% acetonitrile) at 300 nl min-1 over 50 min Ionization was performed on liquid junction with a spray voltage of 1.3 kV applied to non-coated capillary probe (PicoTip EMITER 10 μm tip ID; New Objective). Peptides ions were automatically analyzed by the data dependent method as follows: full MS scan (m/z 300-1600) on Orbitrap analyser and MS/MS on the 4 most abundant precursors on the LTQ linear ion trap. In this study only +2 and +3 charged peptides were subjected to MS/MS experiments with an exclusion window of 1.5 min, with classical peptides fragmentation parameters: Qz=0.22, activation time=50 ms, collision energy=35%.

The raw data produced on LTQ-Orbitrap mass spectrometer were first converted in mzXML file with ReADW (See the web site sashimi sourceforge.net) and in a second step, protein identification was performed with X!Tandem software (X!Tandem tornado 2008.02.01.3, (See the web site www.thegpm.org) against a protein database of *S. thermophilus* LMD-9 (GenBank: CP000419.1), associated to a proteomic contaminant database. The X!Tandem search parameters were: trypsin specificity with one missed cleavage, fixed alkylation of cysteine and variable oxidation of methionine. The mass tolerance was fixed to 10 ppm for precursor ions and 0.5 Da for fragment ions. For all proteins identified with a protein E-value<0.01 in the first step, we searched for additional peptides to reinforce identification using similar parameters except that semi-tryptic peptides and protein N-terminal acetylations were accepted. All peptides identified with an E-value<0.1 were conserved. All results for each piece of gel were merged with an home-made program written in java by Benoit Valot at the PAPPSO platform (See the web site moulon.inra.fr/PAPPSO). The final search results were filtered using a multiple threshold filter applied at the protein level and consisting of the following criteria: protein E-value<10-8 identified with a minimum of two different peptides sequences, detected in at least one piece of gel, with an peptide E-value<0.05.

We focused our attention on proteins that were detected in the extracts prepared from strain LMD-9 and that completely disappeared in the extracts prepared from strain TIL883. The identified proteins are disclosed in the Table I.

For each protein detected, we calculated an abundance factor defined as the total number of spectra detected per protein in each gel lane normalized by the theoretical number of peptides having a mass ranging between 800 and 2500 Da. Proteins that were detected in the two repetitions performed for strain LMD-9 and absent in the two repetitions performed for strain TIL883 (abundance factor=0) were taken into account.

TABLE I

| GenBank | MW | Protein identification | Abundance factor[a] LMD-9 | TIL883 |
|---|---|---|---|---|
| Proteins essential for natural transformation[b] | | | | |
| STER1521 | 24400 | DNA uptake protein or related DNA-binding protein, ComEA | 0.63-0.50 | 0-0 |
| STER0922 | 31100 | Predicted Rossmann fold nucleotide-binding protein involved in DNA uptake, DprA | 1.12-1.12 | 0-0 |
| STER1821 | 14700 | Single-stranded DNA-binding protein, SsbB | 0.50-0.83 | 0-0 |
| STER1840 | 11800 | Competence protein ComGC | 1-1.75 | 0-0 |
| STER1841 | 33800 | Type II secretory pathway/competence component, ComGB | 0.64-0.82 | 0-0 |
| STER1842 | 35300 | Type II secretory pathway/competence component, ATPase, ComGA | 0.95-0.79 | 0-0 |
| STER0189 | 20100 | ComX | 0.57-0.14 | 0-0 |
| Proteins induced by the competence state but not essential for transformation[b] | | | | |
| STER0057 | 30100 | Surface antigen, CbpD | 0.75-0.75 | 0-0 |
| STER1430 | 25700 | DNA repair protein, RadC | 0.25-0.33 | 0-0 |
| Subunits of the Ami oligopeptide transport system | | | | |
| STER_1407 | 34600 | ABC-type dipeptide/oligopeptide/nickel transport system, permease component, AmiD | 2.17-2.33 | 0-0 |
| STER_1408 | 55500 | ABC-type dipeptide/oligopeptide/nickel transport system, permease component, AmiC | 1.41-1.12 | 0-0 |
| STER_1406 | 39800 | ABC-type dipeptide/oligopeptide/nickel transport system, ATPase component, AmiE | 1.28-1. | 0-0 |
| Other proteins | | | | |
| STER_1356 | 50500 | Radical SAM superfamily enzyme | 1.55-1.65 | 0-0 |
| STER_1652 | 50300 | lactococcin A ABC transporter permease protein, PcsB | 0.60-1.00 | 0-0 |
| STER_0329 | 32200 | Urease accessory protein UreH | 0.57-0.57 | 0-0 |
| STER_0123 | 18500 | Predicted RNA-binding protein containing a PIN domain | 0.60-0.40 | 0-0 |
| STER_1296 | 45700 | Permease of the major facilitator superfamily | 0.57-0.29 | 0-0 |
| STER_0331 | 29100 | ABC-type cobalt transport system, permease component CbiQ or related transporter | 0.23-0.46 | 0-0 |

TABLE I-continued

| GenBank | MW | Protein identification | Abundance factor[a] | |
|---|---|---|---|---|
| | | | LMD-9 | TIL883 |
| STER_1779 | 12200 | Thioredoxin domain containing protein | 0.33-0.33 | 0-0 |
| STER_1834 | 43200 | Acetate kinase | 0.26-0.32 | 0-0 |

[a]The abundance factor is the ratio between the total number of spectra obtained during the protein identification process on the theoretical number of peptides ranging between 800 and 2500 Da. Two repetitions were performed for each strain leading to two values.

The results show that in addition to the subunits C, D and E of the Ami transporter, which were absent from the mutant, as expected, seventeen proteins fulfilled this criterion (Table I). Eight were encoded by genes the orthologues of which were identified as late CSP-induced genes in *S. pneumoniae*. Among them, six have also been identified as essential for natural transformation (Peterson et al., Identification of competence pheromone responsive genes in *Streptococcus pneumoniae* by use of DNA microarrays. Mol. Microbiol. 51:1051-1070, 2004). The ComX protein involved in the regulation of the competence state was also detected in strain LMD-9 but not in strain TIL883.

These results suggest that the Ami transporter is involved in the regulatory pathway that controls the induction of the competence state in *S. thermophilus* and also that natural transformation can be turned on in CDM during the exponential growth phase.

2) The *S. thermophilus* LMD-9 is Naturally Transformable in CDM

To check the hypothesis formulated on the basis of our proteomic results, we first tested the natural transformability of *S. thermophilus* using the pG+host9 plasmid.

An overnight culture of strain LMD-9 grown in CDM at 42° C. was diluted in CDM to $OD_{600}$ 0.05. 2 ml of this diluted culture were distributed in 2-ml tubes and incubated in a water bath at 42° C. Once each hour for four hours, a sample was used to measure the $OD_{600}$ and 100 µl were mixed with 1 µg of plasmid DNA. Cells with DNA were incubated for 2 hours at 28° C. before being plated on M17 medium (DIFCO) supplemented with 10 g liter-1 lactose (M17lac) with erythromycin (5 µg ml-1 for *S. thermophilus*).

Figure 1:
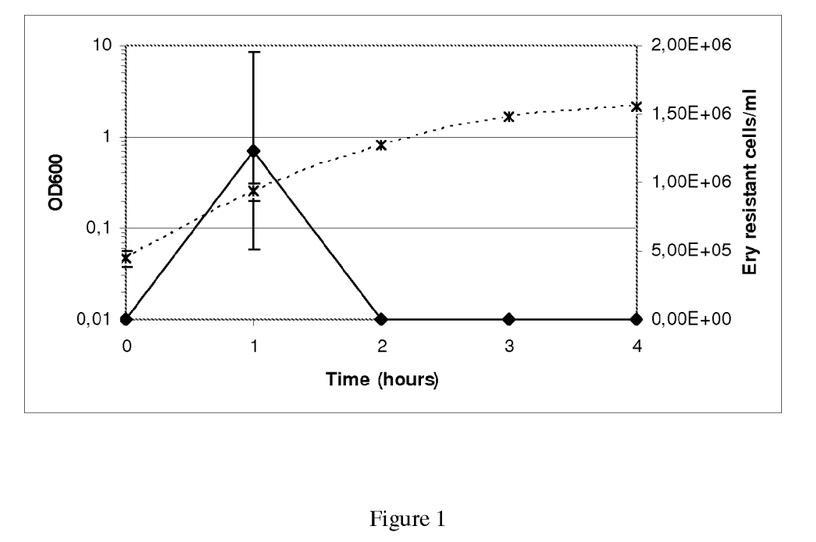
FIG. 1: Development of competence during growth of strain LMD-9 in CDM using pG+host9 plasmid as transformant DNA.

The FIG. 1 shows the development of competence during growth of strain LMD-9 in CDM using pG+host9 plasmid as transformant DNA. Optical density ($OD_{600}$) (×, dashed line) was used to measure cell numbers and count of cells resistant to erythromycin (Ery resistant cells) (♦, plain line) was used to assess competence. 1 µg of plasmid DNA was mixed with 100 µl of cells. The mean of three independent experiments are presented and error bars indicate standard deviation.

We obtained erythromycin resistant cells (transformants) but only in samples harvested one hour after dilution (FIG. 1). We observed a mean of 1.2×106 transformants per ml (standard error, ±7.2×105 transformants per ml; n=3). The presence of the plasmid pG+host9 in these bacteria was checked on several colonies by PCR.

This result indicates that bacteria were able to take up the plasmid but only at a specific growth stage corresponding to the beginning of the exponential phase ($OD_{600}$ 0.2-0.3).

To confirm the transformability of *S. thermophilus*, to demonstrate its ability to take up linear DNA (PCR fragment or chromosomal DNA) and to incorporate it by homologous recombination in its chromosome and also to assess the kinetics of the transformation rate more precisely, we needed chromosomal DNA containing an antibiotic resistant marker.

For that purpose, we constructed strain TIL1192 (LMD-9 feoB::erm) containing an erythromycin (erm) resistant cassette introduced into the chromosome of strain LMD-9 at the feo locus. Integration of a PCR fragment by homologous recombination in the chromosome of strain LMD-9 was demonstrated in the framework of this construction.

Chromosomal DNA of strain TIL1192 was further used as donor DNA to study the timing of the triggering of the competence state during growth in CDM.

An overnight culture of strain LMD-9 grown in CDM at 42° C. was diluted in CDM to $OD_{600}$ 0.05. 2 ml of this diluted culture were distributed in 2-ml tubes and incubated in a water bath at 42° C. Once twenty minutes for two hours, a sample was used to measure the $OD_{600}$ and 100 µl were mixed with 1 µg of chromosomal DNA. Cells with DNA were incubated for 2 hours at 42° C. before being plated on M17 medium (DIFCO) supplemented with 10 g liter-1 lactose (M17lac) with erythromycin (5 µg ml-1 or kanamycin 1000 µg/ml-1 for *S. thermophilus*).

Figure 2:
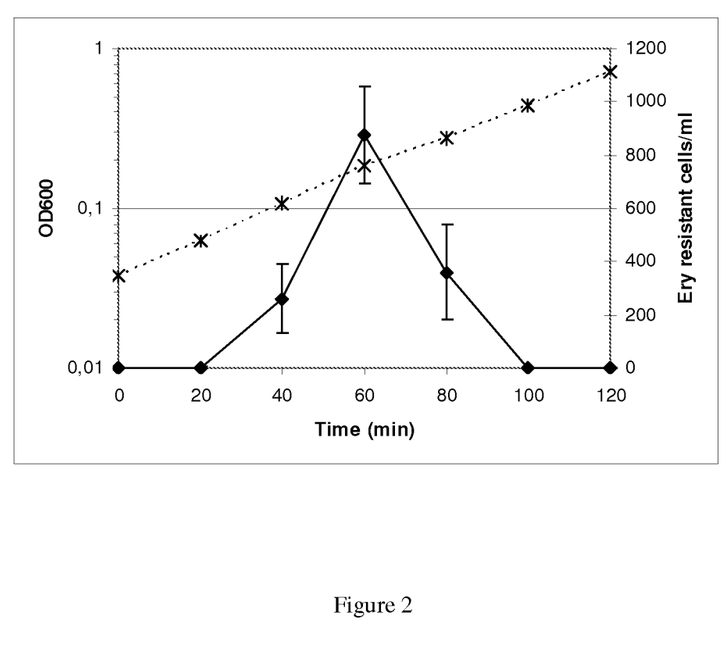
FIG. 2: Development of competence during growth of strain LMD-9 in CDM using chromosomal DNA of strain TIL1192 as transformant DNA.

The FIG. 2 shows the development of competence during growth of strain LMD-9 in CDM using chromosomal DNA of strain TIL1192 as transformant DNA. Optical density ($OD_{600}$) (×, dashed line) was used to measure cell number and count of cells resistant to erythromycin (Ery resistant cells) (♦, solid line) was used to assess competence. 1 µg of chromosomal DNA was mixed with 100 µl of cells. The mean of four independent experiments are presented and error bars indicate standard deviation.

The kinetics of transformation obtained from four independent experiments (FIG. 2) confirmed that natural competence is a short transitory state. Transformability rose sharply 20 min after dilution ($OD_{600}$ 0.06), reached an optimum one hour after dilution ($OD_{600}$ 0.17~0.2) and then rapidly declined. One hundred min after dilution ($OD_{600}$ 0.4~0.5), cells were no longer transformable. At the optimum, the average transformation rate was 3.8 10-6 (standard error, ±4.6 10-7; n=4).

We also tested the transformability of strain TIL883 (ΔamiCDE) with chromosomal DNA of TIL1192 under the same conditions. No transformants were obtained during the growth of this strain in CDM.

In order to confirm that antibiotic resistant clones obtained from the previous experiments were the result of a natural transformation involving ComEC and most probably a transformasome complex similar to the one described in *S. pneumoniae*, we constructed strain TIL1195 (LMD-9 comEC::erm). ComEC is one of the proteins of the DNA uptake machinery essential for natural transformation in *S. pneumoniae* and *B. subtilis*.

We also constructed TIL1193 (LMD-9 feo::aphA3) as a chromosomal DNA source with a different antibiotic resistance than erythromycin. We checked that natural transformation of strain LMD-9 with chromosomal DNA of strain TIL1193 gave a similar transformation rate as with chromosomal DNA of strain TIL1192 (data not shown). Finally, we tried to naturally transform strain TIL1195 with chromosomal DNA of strain TIL1193. Samples of cells of TIL1195 grown in CDM were harvested every 30 min for 2 hours and tested for transformation.

We obtained no kanamycin-resistant clones.

In order to confirm that ComX is essential for natural transformation in *S. thermophilus*, we constructed strain TIL1196 (LMD-9 comX::erm). Samples of cells of TIL1196 grown in CDM were harvested every 30 min for 2 hours and tested for transformation with chromosomal DNA of strain TIL1193.

As expected, we obtained no kanamycin-resistant clones during this kinetic.

Finally, we have found a natural condition of growth that turns on the transformability of strain LMD-9. Using plasmid or chromosomal DNA as donor DNA, we showed that cells were transformable in CDM, during a narrow window, the optimum being one hour after the dilution of an overnight culture in CDM. The rates obtained made it possible to easily construct deletion mutants using PCR fragments and were much higher with plasmid DNA than with chromosomal DNA. This difference can be explained by two factors. First, the higher number of molecules of plasmid compared to the number of molecules of chromosome present in 1 µg DNA (around 450 fold more). Second, the pG+host plasmids generate linear plasmid multimers in *Lactococcus lactis* (Maguin et al., Efficient insertional mutagenesis in lactococci and other gram-positive bacteria. J. Bacteriol. 178:931-935, 1996). Such is probably also the case in *S. thermophilus*.

3) The Ami Transporter Indirectly Controls the Transcription of Genes Necessary for the Development of Competence in Streptococci Among the proteins detected in strain LMD-9 and not in strain TIL883, three were chosen for a transcriptional study of the corresponding genes. These proteins were ComGA that is involved in the pore assembly, DprA, a recombination mediator protein that conveys incoming ssDNA to the recombinase RecA and the sigma factor ComX. Although the abundance factor of RecA did not reach zero in the strain TIL883 but decreased by a factor 4 (data not shown), we chose to follow its encoding gene because RecA is essential for transformation in many Gram-positive transformable species.

Figure 3:
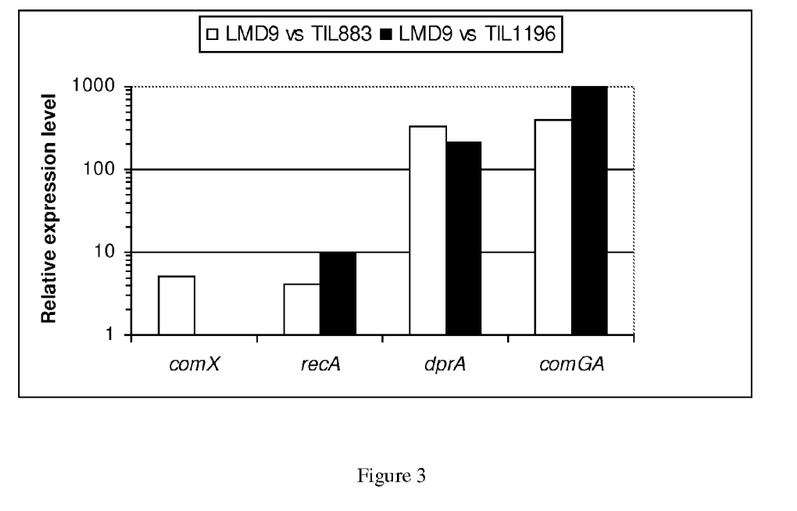
FIG. 3: Relative expression levels of comX, recA, dprA and comGA between *S. thermophilus* LMD-9 and strain TIL883 (LMD9 ΔamiCDE) or strain TIL1196 (LMD-9 comX::erm).

The FIG. 3 shows the relative expression levels of comX, recA, dprA and comGA between *S. thermophilus* LMD-9 and strain TIL883 (LMD9 ΔamiCDE) or strain TIL1196 (LMD-9 comX::erm). Relative expression levels were computed using the comparative critical threshold method ($2^{-\Delta\Delta C_T}$) as described by Livak and Schmittgen (Analysis of relative gene expression data using real-time quantitative PCR and the 2(-ΔΔC(T)) Method. Methods, 25:402-408, 2001). Data are expressed as means from three independent experiments and were significant according to an analysis of variance (P<0.05).

As shown in FIG. 3, the level of expression of comGA and dprA of strain LMD-9 was higher than that of strain TIL883. To a lesser extent but with significant values (P<0.05), we obtained similar results with comX and recA that were 5-fold and 4-fold more highly expressed in strain LMD-9, respectively.

To confirm that the transcription of genes dprA, comGA and recA is under the control of ComX, we compared the expression of these genes in strain LMD-9 and strain TIL1196 (LMD9 comX::erm). As expected, the transcription of the three genes was significantly higher in strain LMD-9 than in strain TIL1196 (FIG. 3) confirming that their transcription is positively controlled by ComX.

4) The Oligopeptide-Binding Protein AmiA3 Plays the Major Role in the Control of Competence The genome of strain LMD-9 displays only two genes encoding oligopeptide-binding proteins, amiA1 (ster_1409), the first gene of the ami operon (ster_1408 to ster_1405) and amiA3 (ster_1411) that is flanked by two transposase encoding genes.

We constructed three strains, TIL1197 (amiA3::erm), TIL1198 (ΔamiA1) and TIL1199 (amiA3::erm ΔamiA1) corresponding to insertional mutagenesis of amiA3, deletion of amiA1 and a combination of both mutations, respectively.

The transformability of the three strains was tested using chromosomal DNA of strain TIL1193 and compared to that of strain LMD-9 at its optimum of competence, i.e. one hour after the dilution of the cells in CDM.

As expected, no kanamycin resistant cells were obtained after transformation of strain TIL1199. However, the percentage of the competence rate of strains TIL1197 (amiA3::erm) and TIL1198 (ΔamiA1) compared to that of strain LMD-9 were 1% (standard error±2) and 48% (standard error±4), respectively.

This result suggests that AmiA3 is more important in the triggering of the competence than AmiA1.

As our experiments were performed in a medium without peptides, we hypothesize that in *S. thermophilus*, the Ami3 oligopeptide-binding protein imports a peptide involved with a transcriptional regulator in the control of the expression of comX. This peptide could be a specific pheromone or a peptide resulting from the degradation of secreted proteins or proteins released by lysis of bacteria.

5) The Growth Medium Composition Influences the Competence State of *S. thermophilus*

Kinetics of competence rate were performed with LMD-9 cells grown in M17lac and with pG+host9 plasmid DNA or chromosomal DNA of strain TIL1192.

With both types of donor DNA, no erythromycin resistant transformants were obtained with cells harvested every 30 min for 2 hours.

We then compared the expression of comGA, dprA, recA and comX from RNA extracted from LMD-9 cells grown in CDM and M17lac medium and harvested at $OD_{600}$ 0.2.

We observed that these genes were respectively, 1492, 2246, 24 and 236 more highly expressed in CDM than in M17lac which was consistent with the absence of transformants during growth in M17lac.

6) Strains CNRZ1066 and LMG18311 are not Efficiently Transformable in CDM

We tested natural transformability of the two other *S. thermophilus* strains, CNRZ1066 and LMG18311.

For this purpose, we used the plasmid pG+host9 as donor DNA and cells were harvested every 30 min for 2 hours.

We obtained no erythromycin resistant clones with strain CNRZ1066 and a few erythromycin resistant clones with strain LMG18311, one hour after dilution. However, we obtained 2 104 less transformants with strain LMG18311 than with strain LMD-9. We also used chromosomal DNA of strain TIL1195 (LMD-9 comEC::erm) as donor DNA because surrounding regions of gene comEC are highly conserved between strains LMD-9, CNRZ1066 and LMG18311 (more than 98% identity over 5 kb upstream and downstream comEC). Under this condition, we obtained no erythromycin resistant clones with both strains.

7) Identification of a Competence Stimulating Peptide in S. thermophilus

During the proteomic approach described in paragraph 1, we noticed that the synthesis of a transcriptional regulator annotated PlcR, ster0316, decreased in the Ami mutant compared to the wild type strain. These regulators are known to be regulated by peptides that are secreted and imported back by Opp. As we suspected that the triggering of the competence state in S. thermophilus is controlled by a secreted peptide further imported by Opp also called Ami in this species, we thought that this regulator could be involved in the mechanism controlling the triggering of competence in S. thermophilus. We deleted ster0316 and replaced it by an erythromycin resistance cassette. The transformability of the mutant was assessed for three hours every thirty minutes using chromosomal DNA of strain TIL1193 (feo::aphA3). Three independent experiments were performed and no kanamycin resistant transformants were obtained indicating that ster0316 is involved in the triggering of competence in S. thermophilus.

A small CDS, papR-like, is located downstream of gene ster0316 and is not annotated in Genbank. As the activity of PlcR regulators is controlled by peptides, we suspected that the peptide encoded by this small papR-like CDS could be involved in the control of the activity of Ster0316. papR-like was deleted and replaced by a spectinomycin resistance cassette leading to the construction of a papR-like::spec mutant. The transformability of the mutant was assessed for three hours every thirty minutes using plasmid DNA (pGhost9). Four independent experiments were performed and no erythromycin resistant transformants were obtained indicating that papR-like is most probably involved in the triggering of competence in S. thermophilus probably through the control of the activity of Ster0316.

In order to check that the absence of transformability of the papR-like::spec mutant was the result of the absence of the papR-like gene and not the result of a polar effect of the presence of the spectinomycin resistant cassette on upstream or downstream genes of papR-like, we cloned the papR-like gene in a plasmid in order to express it under the control of a strong constitutive promoter and introduced this plasmid by electroporation in the papR-like::spec mutant. The transformability of the mutant was assessed one hour after the dilution of the preculture in CDM using plasmid DNA (pGhost9::kana). We obtained kanamycin resistant transformants indicating that the transformability of the papR-like::spec mutant was restored by the presence of papR and that the absence of transformability of the papR-like::spec mutant was the result of the absence of the papR-like gene.

8) Protocol of Induction of Competence and Transformation of S. thermophilus Comprising Medium CDM and CSP (Competence Stimulating Peptide)

As used herein, CSP refers to Pap-R like peptide or a fragment thereof.

S. thermophilus cells are grown overnight at 42° C. in CDM. The culture is then diluted in CDM at an $OD_{600}$ 0.05. Sixty minutes after dilution, the competence stimulating peptide (CSP), which is the mature peptide comprising SEQ ID No1 or fragments or derivatives of SEQ ID No1 that allow to induce competence in S. thermophilus, is added to the culture at a final concentration of 1 μM. Ten minutes later, 100 μl of the culture containing the CSP is mixed with 1 μg of DNA and incubated for 2 hours at 28° C. when mixed with a thermosensitive replicative plasmid DNA or 1 hour at 42° C. when mixed with chromosomal DNA or PCR fragments, before being serially diluted and spread on M17lac plates with the appropriate antibiotic.

9) Overexpression of the papR-Like Gene Induces the Transformability of Strain LMG18311

Strain S. thermophilus LMG18311 is naturally poorly transformable. We introduced in this strain and by electroporation, the plasmid comprising the sequence SEQ ID No6 coding for the polypeptide derivatives having the sequence SEQ ID No5, plasmid that allows the overexpression of the papR-like gene and that is described in paragraph 7. The transformability of the mutant was assessed one hour after the dilution of the culture of this mutant in CDM using plasmid DNA (pGhost9::kana). 100 μl of the culture was mixed with 1 μg of DNA. Cells were further incubated 2 hours at 30° C. before been spread on M17lac plates containing the appropriate antibiotic. The LMG18311 wild type strain was used as a control. We obtained no kanamycin resistant transformants with the control and many (>1000) with the mutant overexpressing the papR-like gene. This result indicates that the overexpression of the papR-like gene is able to stimulate the transformability of a poorly transformable strain.

10) Transformation of S. thermophilus by a Plasmid that Allows the Overexpression of the papR-Like Gene S. thermophilus cells are electroporated with a replicative plasmid where the papR-like gene is under the control of a strong constitutive promoter. Cells containing this plasmid are grown overnight at 42° C. in CDM. The culture is then diluted in CDM at an $OD_{600}$ 0.05. One hour after dilution, 100 μl of the culture is mixed with 1 μg of DNA and incubated for 2 hours at 28° C. when mixed with a thermosensitive replicative plasmid DNA or 1 hour at 42° C. when mixed with chromosomal DNA or PCR fragments, before being serially diluted and spread on M17lac plates with the appropriate antibiotic. The transformants can further be easily cured of the replicative plasmid by growth in the absence of antibiotic.

11) Identification of Different Fragments of SEQ ID No1

SEQ ID No1 is the precursor of shorter peptides that are secreted. These shorter peptides, corresponding to fragments of SEQ ID No1, are active peptides that trigger the competence state in S. thermophilus.

For identifying the sequence of these shorter active peptides, the inventors have used two strains, one that is deleted for the papR-like gene (referred as "deleted strain" thereafter) and one that overexpresses the papR-like gene and that is unable to import peptides because deleted for the genes encoding the oligopeptide transporter Ami (referred as "overproducing strain" thereafter). In the overproducing strain, the sequence of the peptide that is overproduced is SEQ ID No5.

Using LC-MS/MS analysis, the inventors have searched for peptide masses corresponding to fragments of SEQ ID No1 in the culture supernatant of the overproducing strain that were absent in that of the deleted strain. Culture supernatants were treated in order to be enriched in peptides with the following method:
(1) ultrafiltration (10 kDa cut-off),
(2) injection of the ultrafiltrate (<10 kDa) on Sep-pack C18 with a 30% acetonitrile washing step and a 40% acetonitrile elution step.
Eluted fractions were further dried and resuspended with 0.1% trifluoroacetic acid 2% acetonitrile.

Three masses corresponding to masses of five different fragments of SEQ ID No1 (present in the overproducing strain and absent in the deleted strain) have been identified, with different retention times (Rt) during the HPLC runs (A—natural peptides, below). The inventors thus identified sequences of fragments of SEQ ID No1 that match with the m/z measurements.

The results are shown herebelow:

|  | m/z (z=1) | Rt (min) | Identified Sequences | SEQ ID No | Competence |
|---|---|---|---|---|---|
| A-Natural peptides | 1180.6434 | 45.83 | IAILPYFAGCL | 7 | YES |
|  |  |  | LIAILPYFAGC | 8 | NT |
|  | 1067.5594 | 42.58 | AILPYFAGCL | 9 | NT |
|  |  |  | IAILPYFAGC | 10 | NT |
|  | 996.5223 | 40.58 | ILPYFAGCL | 11 | NT |
| B-Alkylated peptides | 1237.6649 | 42.98 | IAILPYFAGC*L | — | NO |
|  |  |  | LIAILPYFAGC* | — | NT |
|  | 1124.5808 | 39.72 | AILPYFAGC*L | — | NT |
|  |  |  | IAILPYFAGC*L | — | NT |
|  | 1053.5437 | 37.66 | ILPYFAGC*L | — | NT |

NT, not tested
*alkylated form of the cysteine

At this step, peptide ion fragmentation was not possible due to the weakness of the mass spectrometry signals. In order to confirm the presence of a cysteine residue in the different fragments, alkylation of the supernatants of the deleted and the overproducing strains was performed with iodoacetamide with the following protocol: 150 µl of NaOH 5M were added to 30 ml of supernatant. Alkylation was performed with iodoacetamide at a final concentration of 20 mM for 30 min in the dark. Samples were enriched in peptides as described above with the following modification, 50 µl of formic acid was added to adjust the pH to 6.5 after the ultrafiltration step.

Masses corresponding to alkylated forms of all fragments (B—alkylated peptides) were detected, with the expected shift in HPLC retention times, in the supernatant of the overproducing strain and not detected in the deleted strain confirming that these fragments contain a cysteine amino acid.

Alkylation increased the peptide signals in mass spectrometry and allowed the fragmentation of the longer one. Fragmentation of the peptide validated the IAILPYFAGCL sequence of the 1237,6649 mass (SEQ ID No7).

In conclusion, the inventors have shown that SEQ ID No1 is the precursor of peptides that are secreted in the supernatant of the overproducing S. thermophilus LMD9 strain. The inventors identified 3 masses corresponding to 5 different fragments of SEQ ID No1. The inventors validated the amino acids sequence SEQ ID No7 (IAILPYFAGCL), which is an active competence peptide. The inventors have also showed that the shorter sequences are products of degradation of SEQ ID No7 by proteases and/or aminopeptidases.

12) Biologic Activity of Fragments of SEQ ID No1

The inventors tested the activity of fragments of SEQ ID No1 using a strain deleted for the papR gene using the protocol described in part 8. The inventors thus synthesized different fragments of SEQ ID No1 in order to test their biological activity. Fragments were synthesized as below:

IAILPYFAGCL  SEQ ID No 7

LPYFAGCL  SEQ ID No 12

PYFAGCL  SEQ ID No 13

To test the biological activity of those fragments, peptides were added to a culture of a strain deleted for the papR gene at a final concentration of 1 µM, 1 hour after the dilution of the culture at an $OD_{600}$ of 0.05 in a chemical defined medium (CDM). Transformation assays were performed with 100 µl of cells with 1 µg of plasmid and or chromosomal DNA.

The results are disclosed herebelow.

The numbers of transformants obtained with 100 µl of competent cells are as follow:

| Transforming DNA | SEQ ID N°7 | SEQ ID N°12 | SEQ ID N°13 |
|---|---|---|---|
| Chromosomal | 24 | 41 | 0 |
| Plasmid | $284\,10^2$ | $780\,10^2$ | 0 |

Cysteyl residue is a reactive amino acid due to the presence of a free SH. In order to test the significance of this residue in the biological activity of the peptide, SEQ ID No7 was alkylated, as described above, and its activity was tested.

The numbers of transformants obtained with 100 µl of competent cells are as follow:

| Transforming DNA | SEQ ID N°7 | Alkylated SEQ ID N°7 |
|---|---|---|
| Chromosomal | 35 | 0 |
| Plasmid | $70\,10^2$ | 2 |

These results indicate that SEQ ID No7 needs to have a free cysteyl residue to be active and that the oxido-reduction state or the alkylation of the peptide influence the competence rate of S. thermophilus strains.

S. thermophilus strain LMG18311 is naturally poorly competent and strain CNRZ1066 is naturally not competent. However, complementation of both strains with a plasmid that overexpresses the papR gene makes them competent. The inventors tested the effect of the addition of SEQ ID No7 on the competence of both strains in the same condition as described above for the LMD9 strain.

The numbers of transformants obtained with 100 µl of competent cells are as follow:

| Transforming | LMG18311 | | CNRZ1066 | |
|---|---|---|---|---|
| DNA | No Fragment | SEQ ID N°7 | No Fragment | SEQ ID N°7 |
| Chromosomal | 0 | 477 | 0 | 0 |
| Plasmid | 7 | 731 10³ | 0 | 274 10³ |

These results indicate that the addition of SEQ ID No7 in a culture of *S. thermophilus* strain CNRZ1066 or LMG18311 renders them competent.

The inventors have thus shown that SEQ ID No1 and fragments of SEQ ID No1 (particularly SEQ ID No7) are capable of stimulating competence in *Streptococcus*.

The invention claimed is:

1. A method for producing a mutant bacterium of the phylum *Firmicutes* which comprises the steps of:
   (a) producing transformation competent bacteria of the phylum *Firmicutes* comprising contacting said bacteria with an effective amount of a polypeptide comprising the amino acid sequence of SEQ ID NO: 1 (LKTLKIFVLFSLLIAILPYFAGCL), a derivative thereof having a percentage of identity of at least 90% with the amino acid sequence SEQ ID NO: 1; or a fragment of SEQ ID NO: 1, wherein said derivative or fragment is capable of stimulating competence in *Streptococcus*; and
   (b) contacting said transformation competent bacteria with homologous DNA comprising a mutation under conditions allowing transformation by homologous recombination of said bacteria with said homologous DNA comprising said mutation to produce said mutant bacterium.

2. The method of claim 1 wherein the polypeptide consists of the amino acid sequence of SEQ ID NO: 12.

3. The method of claim 2 wherein said contacting of step (a) comprises culturing said bacteria in a peptide-free medium and adding the effective amount of the polypeptide to the peptide-free medium.

4. The method of claim 1 wherein the bacteria are of the genus *Streptococcus*.

5. The method of claim 1, wherein the polypeptide consists of the amino acid sequence of SEQ ID NO: 1 or of a derivative thereof having a percentage of identity of at least 90% with the amino acid sequence of SEQ ID NO: 1.

6. The method of claim 1, wherein the polypeptide consists of the amino acid sequence of SEQ ID NO: 1.

7. The method of claim 1, wherein the length of the polypeptide is less than 100 amino acids.

8. The method of claim 1, wherein the polypeptide further comprises an amino acid sequence corresponding to a signal peptide.

9. The method of claim 1, wherein said step of producing transformation competent bacteria is performed in a culture medium comprising an effective amount of said polypeptide.

10. The method of claim 1, wherein the bacteria are of the genus *Streptococcus*.

11. The method of claim 1, wherein the bacteria are of the species *Streptococcus thermophilus*.

12. The method of claim 1, wherein said contacting of step (a) comprised expression in said bacteria of a nucleotide sequence encoding a polypeptide comprising the amino acid sequence of SEQ ID NO: 1 (LKTLKIFVLFSLLIAILPYFAGCL) a derivative thereof having a percentage of identity of at least 90% with the amino acid sequence SEQ ID NO: 1; or a fragment of SEQ ID NO: 1, wherein said derivative or fragment is capable of stimulating competence in *Streptococcus* and wherein the nucleotide sequence encoding the polypeptide is operably linked to a gene expression sequence functional in said bacterium.

13. The method of claim 12, wherein the gene expression sequence comprises a constitutive promoter or an inducible promoter.

14. The method of claim 12, wherein the polypeptide consists of the amino acid sequence of SEQ ID NO: 1 or of a derivative thereof having a percentage of identity of at least 90% with the amino acid sequence of SEQ ID NO: 1.

15. The method of claim 12, wherein the polypeptide consists of the amino acid sequence of SEQ ID NO: 1.

16. The method of claim 12, wherein the nucleotide further encodes a signal peptide.

17. The method of claim 1, wherein said contacting of step (a) comprises culturing said bacteria in a peptide-free medium and adding the effective amount of the polypeptide to the peptide-free medium.

18. The method of claim 1, wherein the contacting of step (a) comprises the steps of (i) culturing said bacteria in a peptide-free medium to an OD600 between 1.5 and 2.5 and (ii) diluting the culture of step (i) to an OD600 between 0.01 and 0.1 prior to adding the effective amount of the polypeptide to the growth medium.

* * * * *

SEQUENCE LISTING

<160> NUMBER OF SEQ ID NOS: 13

<210> SEQ ID NO 1
<211> LENGTH: 24
<212> TYPE: PRT
<213> ORGANISM: Streptococcus thermophilus

<400> SEQUENCE: 1

Leu Lys Thr Leu Lys Ile Phe Val Leu Phe Ser Leu Leu Ile Ala Ile
1               5                   10                  15

Leu Pro Tyr Phe Ala Gly Cys Leu
            20

<210> SEQ ID NO 2
<211> LENGTH: 75
<212> TYPE: DNA
<213> ORGANISM: Streptococcus thermophilus

<400> SEQUENCE: 2
ttgaaaaccc tgaaaatatt tgtactattt tcactactta ttgctatctt gccttatttt      60
gcaggatgtc tttaa                                                      75

<210> SEQ ID NO 3
<211> LENGTH: 22
<212> TYPE: DNA
<213> ORGANISM: Artificial sequence
<220> FEATURE:
<223> OTHER INFORMATION: Sequence recognized by PlcR like

<400> SEQUENCE: 3
atagtgacat atatgtctct at                                              22

<210> SEQ ID NO 4
<211> LENGTH: 22
<212> TYPE: DNA
<213> ORGANISM: Artificial sequence
<220> FEATURE:
<223> OTHER INFORMATION: sequence recognized by PlcR like

<400> SEQUENCE: 4
gtggtgacat aaatgtcact at                                              22

<210> SEQ ID NO 5
<211> LENGTH: 25
<212> TYPE: PRT
<213> ORGANISM: Artificial sequence
<220> FEATURE:
<223> OTHER INFORMATION: Derivative polypeptide of SEQ ID N01

<400> SEQUENCE: 5

Met Gly Lys Thr Leu Lys Ile Phe Val Leu Phe Ser Leu Leu Ile Ala
1               5                   10                  15

Ile Leu Pro Tyr Phe Ala Gly Cys Leu
            20                  25

<210> SEQ ID NO 6
<211> LENGTH: 78
<212> TYPE: DNA
<213> ORGANISM: Artificial sequence
<220> FEATURE:
<223> OTHER INFORMATION: nucleic acid sequence coding for the
      polypeptide SEQ ID N05

<400> SEQUENCE: 6
atggggaaaa ccctgaaaat atttgtacta ttttcactac ttattgctat cttgccttat     60
tttgcaggat gtctttaa                                                   78

<210> SEQ ID NO 7
<211> LENGTH: 11
<212> TYPE: PRT
<213> ORGANISM: Streptococcus thermophilus

<400> SEQUENCE: 7

Ile Ala Ile Leu Pro Tyr Phe Ala Gly Cys Leu
1               5                   10

<210> SEQ ID NO 8
<211> LENGTH: 11
<212> TYPE: PRT
<213> ORGANISM: Streptococcus thermophilus

<400> SEQUENCE: 8

Leu Ile Ala Ile Leu Pro Tyr Phe Ala Gly Cys
1               5                   10

<210> SEQ ID NO 9
<211> LENGTH: 10
<212> TYPE: PRT
<213> ORGANISM: Streptococcus thermophilus

<400> SEQUENCE: 9

Ala Ile Leu Pro Tyr Phe Ala Gly Cys Leu
1               5                   10

<210> SEQ ID NO 10
<211> LENGTH: 10
<212> TYPE: PRT
<213> ORGANISM: Streptococcus thermophilus

<400> SEQUENCE: 10

Ile Ala Ile Leu Pro Tyr Phe Ala Gly Cys
1               5                   10

<210> SEQ ID NO 11
<211> LENGTH: 9
<212> TYPE: PRT
<213> ORGANISM: Streptococcus thermophilus

<400> SEQUENCE: 11

Ile Leu Pro Tyr Phe Ala Gly Cys Leu
1               5

<210> SEQ ID NO 12
<211> LENGTH: 8
<212> TYPE: PRT
<213> ORGANISM: Artificial sequence
<220> FEATURE:
<223> OTHER INFORMATION: Fragment of SEQ ID N07

<400> SEQUENCE: 12

```
Leu Pro Tyr Phe Ala Gly Cys Leu
1               5

<210> SEQ ID NO 13
<211> LENGTH: 7
<212> TYPE: PRT
<213> ORGANISM: Artificial sequence
<220> FEATURE:
<223> OTHER INFORMATION: Fragment of SEQ ID N07

<400> SEQUENCE: 13

Pro Tyr Phe Ala Gly Cys Leu
1               5
```